(12) United States Patent
Safai et al.

(10) Patent No.: US 7,312,454 B2
(45) Date of Patent: Dec. 25, 2007

(54) NON-DESTRUCTIVE INFRARED INSPECTION DEVICE

(75) Inventors: Morteza Safai, Seattle, WA (US); Gary E. Georgeson, Federal Way, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/259,009

(22) Filed: Oct. 26, 2005

(65) Prior Publication Data

US 2006/0043303 A1  Mar. 2, 2006

Related U.S. Application Data

(63) Continuation-in-part of application No. 10/752,890, filed on Jan. 7, 2004, now Pat. No. 7,231,826, which is a continuation-in-part of application No. 10/620,464, filed on Jul. 16, 2003, now Pat. No. 6,722,202.

(51) Int. Cl.
*G01N 21/88* (2006.01)
(52) U.S. Cl. ...................................... 250/347
(58) Field of Classification Search .............. 250/347
See application file for complete search history.

(56) References Cited

U.S. PATENT DOCUMENTS

| | | | |
|---|---|---|---|
| 3,886,362 A * | 5/1975 | Miroshnikov et al. ...... 374/124 |
| 4,010,636 A | 3/1977 | Clark et al. | |
| 4,399,703 A | 8/1983 | Matzuk | |
| 4,557,598 A * | 12/1985 | Ono et al. ............... 356/241.1 |
| 4,790,294 A | 12/1988 | Allred, III et al. | |
| 4,790,624 A | 12/1988 | Van Hoye et al. | |
| 4,846,573 A | 7/1989 | Taylor et al. | |
| 4,848,159 A | 7/1989 | Kennedy et al. | |
| 4,967,092 A * | 10/1990 | Fraignier et al. ...... 250/559.07 |
| 5,055,683 A * | 10/1991 | McCracken ................. 250/334 |
| 5,062,301 A | 11/1991 | Aleshin et al. | |

(Continued)

FOREIGN PATENT DOCUMENTS

EP    0 392 163 A2    10/1990

(Continued)

OTHER PUBLICATIONS

LOTIS Laser Surface Mapping, Surface Inspection Solutions (1 pg.); (2004) http://user996135.sf2000.registeredsite.com/engineer/id2.html; Visited Sep. 2, 2005.

(Continued)

*Primary Examiner*—Constantine Hannaher
(74) *Attorney, Agent, or Firm*—Alston & Bird LLP

(57) ABSTRACT

A non-destructive inspection device has an infrared sensor for infrared thermography inspection of a structure or surface. A rotatable reflector reflects infrared light from an inspected surface to an infrared sensor. An inspecting portion of a non-destructive device is magnetically coupled to an actuating portion of the device for concerted movement of the portions. An inspection device includes both an infrared sensor for infrared imaging and an optical device such as a camera for visible light imaging.

23 Claims, 11 Drawing Sheets

U.S. PATENT DOCUMENTS

| | | | |
|---|---|---|---|
| 5,343,750 | A | 9/1994 | Bashyam |
| 5,373,317 | A | 12/1994 | Salvati et al. |
| 6,180,928 | B1 | 1/2001 | Garrigus |
| 6,605,807 | B2 | 8/2003 | Safai |
| 6,722,202 | B1 | 4/2004 | Kennedy et al. |
| 2003/0222216 | A1* | 12/2003 | Walkenstein ................ 250/330 |
| 2004/0189987 | A1 | 9/2004 | Bondurant et al. |

FOREIGN PATENT DOCUMENTS

| | | |
|---|---|---|
| EP | 0 820 250 B1 | 1/1998 |
| JP | 02017434 A * | 1/1990 |

OTHER PUBLICATIONS

LOTIS Probes, Laser Surface Mapping and Inspection Solu (2 pgs.); (2004) http://user996135.sf2000.registeredsite.com/engineer/id47.html; Visited Sep. 2, 2005.

Inventions & Innovation Success Story—Electro-Optic Inspection of Heat Exchangers (2 pgs.); http://www.eere.energy.gov/inventions/pdfs/quest.pdf; Visited Sep. 2, 2005, date unknown.

Leonard J. Bonnell, Thomas J. Brukilacchio and Dennis C. Leiner; *A Novel Visible/Infrared Borescope Imaging System for Industry and Surgery (Second Generation)*; SPIE; Jul. 1998; pp. 295-304; vol. 3436.

* cited by examiner

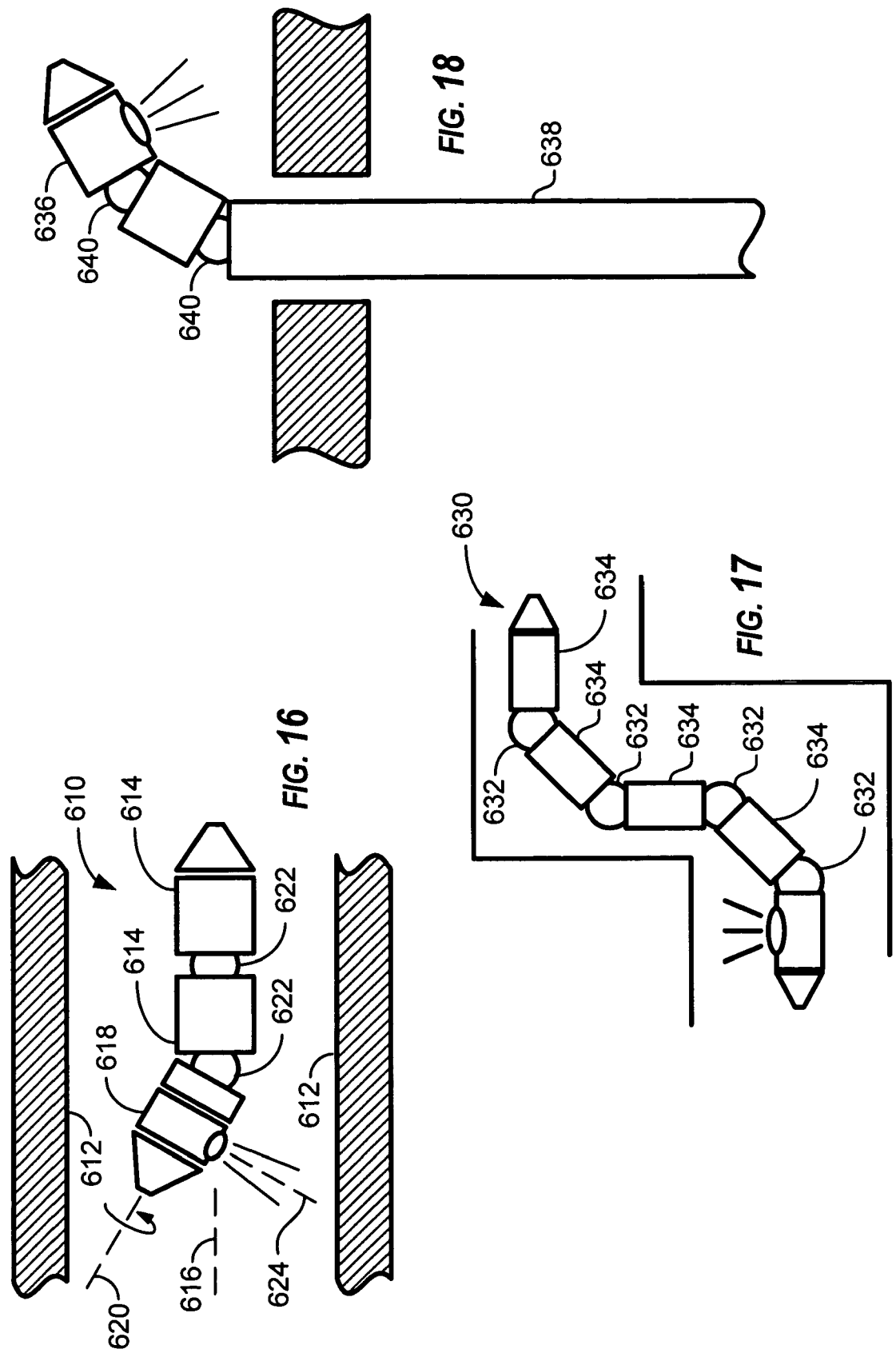

NON-DESTRUCTIVE INFRARED INSPECTION DEVICE

CROSS-REFERENCE TO RELATED APPLICATIONS

This application is a continuation-in-part, and claims the benefit of priority to, U.S. non-provisional patent application No. 10/752,890 of Bossi et al., filed Jan. 7, 2004 now U.S. Pat. No. 7,231,826, which co-pending patent application and the publication thereof, namely United States patent application publication number US2005/0145033A1, published Jul. 7, 2005, are incorporated herein by reference.

FIELD OF THE INVENTION

Embodiments of the present invention relate generally to non-destructive inspection devices. More particularly, embodiments of the invention relate to devices for the infrared inspection of a structure.

BACKGROUND OF THE INVENTION

Manufacturers often optimize the designs of parts that they manufacture in efforts to increase the efficiencies of devices and structures in which the parts are used. Designs are often optimized through the use of light-weight materials and by the minimization of the amounts of materials used.

For example, in order to reduce weight of aircraft components, manufacturers typically design skeletal frames enclosed by thin skins utilizing light-weight materials such as aluminum, titanium, and silicon. In order for these components to perform as intended, the components must be manufactured without surface irregularities and without hidden flaws. If surface irregularities and flaws hidden below the surface of a component go undetected, the component may fail. Therefore such components are typically subjected to careful inspections both prior to use and during the service life of the components.

Aircraft components made of light-weight composite materials are further examples of parts that are routinely subjected to inspection. Composite materials are commonly used because of their engineering qualities, design flexibilities, and low weights. However, a component constructed of a composite material may have flaws both at the surface and below the surface of the material. Surface irregularities such as scratches and holes and more hidden irregularities such as cracks, voids, disbonds, and hidden porosities may greatly compromise the strength and durability of a composite component.

Complicating the inspection of aircraft components and parts for other assemblies is the fact that optimized designs often include complex geometries, curved surfaces, and limited access spaces. For example, a typical aircraft fuselage stringer can be over one hundred feet long, and typically partially encloses an elongate space having a trapezoidal cross-section that may be merely a foot wide. Aircraft wings typically have internal features, bond lines, and close-out joints that further exemplify designs having complex geometries and limited access spaces. Limited-access spaces, such as those enclosed by close-out joints of aircraft wings, are difficult to fully inspect using contemporary inspection devices.

Thus, as typical design optimization processes rely on the assumption that parts are manufactured to exacting specifications, manufacturers face a difficult challenge in identifying parts that fail to meet specifications while controlling manufacturing and maintenance costs. Non-destructive inspection (NDI) devices and techniques provide for inspections and evaluations of fully or partially assembled parts without compromising the parts.

NDI typically involves thoroughly examining a structure without harming the structure or requiring significant disassembly of the structure. NDI is advantageous for many applications in which thorough inspections of the exteriors and interiors of structures are desired. NDI is commonly utilized in the aircraft industry for inspecting aircraft components for internal or external structural damages. Composite components, critical structural components, and light-weight components of aircraft structures are often subjected to NDI to identify surface irregularities and hidden flaws.

A need exists for convenient and reliable NDI devices that are capable detecting flaws defined in the surface of a component and flaws below the surface of the component. A need exists for NDI devices that are capable of inspecting limited-access features of a structure. A need exists for NDI devices that facilitate visual inspections of structural surfaces in conjunction with inspection techniques that reveal hidden flaws.

BRIEF SUMMARY OF THE INVENTION

Embodiments of the invention may address at least some of the above needs and achieve other advantages. For example, a first aspect of the invention relates to a non-destructive inspection device for inspecting a structure optionally related to an aircraft. The inspection device includes an actuating portion and at least one inspecting portion that are magnetically coupled so that the inspecting portion moves in concert with the actuating portion. The inspecting portion includes an infrared sensor and at least one magnet. The actuating portion also includes at least one magnet so that when the actuating portion is placed on a first surface of the structure and the inspecting portion is positioned on a surface of the structure opposite the first surface, the two portions are magnetically coupled so that movement of the actuating portion causes the inspecting portion to move in concert with the actuating portion without the inspecting portion directly contacting the actuating portion.

The inspection device according to the first aspect of the invention optionally includes an optical borescope. Furthermore, the inspecting portion may optionally include a camera, and in one embodiment, a laser.

A second aspect of the invention relates to a method of inspecting a structure. According to the method, an actuating portion of a non-destructive inspection device is placed on a first surface of the structure, and, an inspecting portion of the non-destructive inspection device is positioned on a surface of the structure opposite the first surface. At least one magnet of the inspecting portion magnetically couples to at least one magnet of the actuating portion. The actuating portion is moved on the surface of the structure such that the inspecting portion is moved in concert with the actuating portion. The inspecting portion includes an infrared sensor that creates an output that is received.

A third aspect of the invention relates to an infrared inspection system that includes an infrared sensor, a rotatable reflector disposed to reflect infrared light from an inspected surface to the infrared sensor, and a display system communicably coupled to the infrared sensor for presenting data related to an output signal of the infrared sensor.

According to the third aspect of the invention, the infrared sensor optionally includes an infrared sensitive array and the display system presents a graphical representation of an infrared image of a structure under inspection. Moreover, the infrared inspection system according to the third aspect of the invention optionally includes a second rotatable reflector and a camera device disposed to collect visible light images of an inspected surface by way of the second rotatable reflector.

BRIEF DESCRIPTION OF THE SEVERAL VIEWS OF THE DRAWINGS

Figure 1:
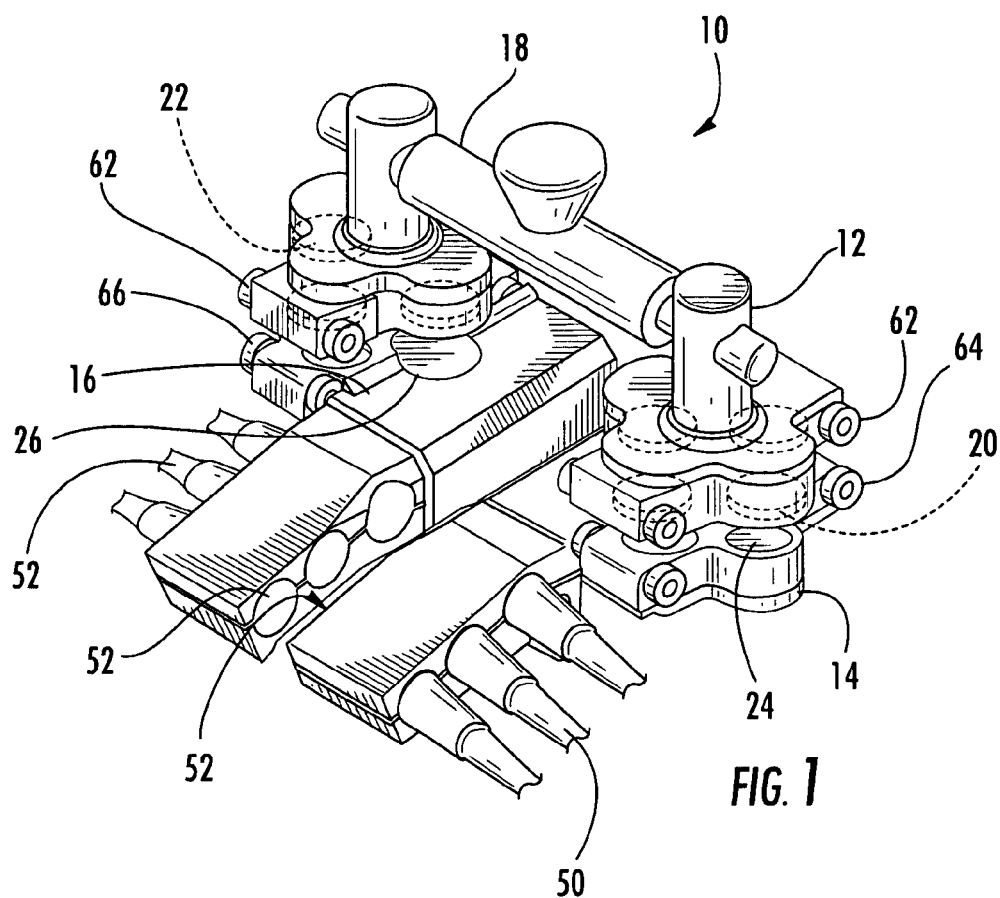
Figure 3:
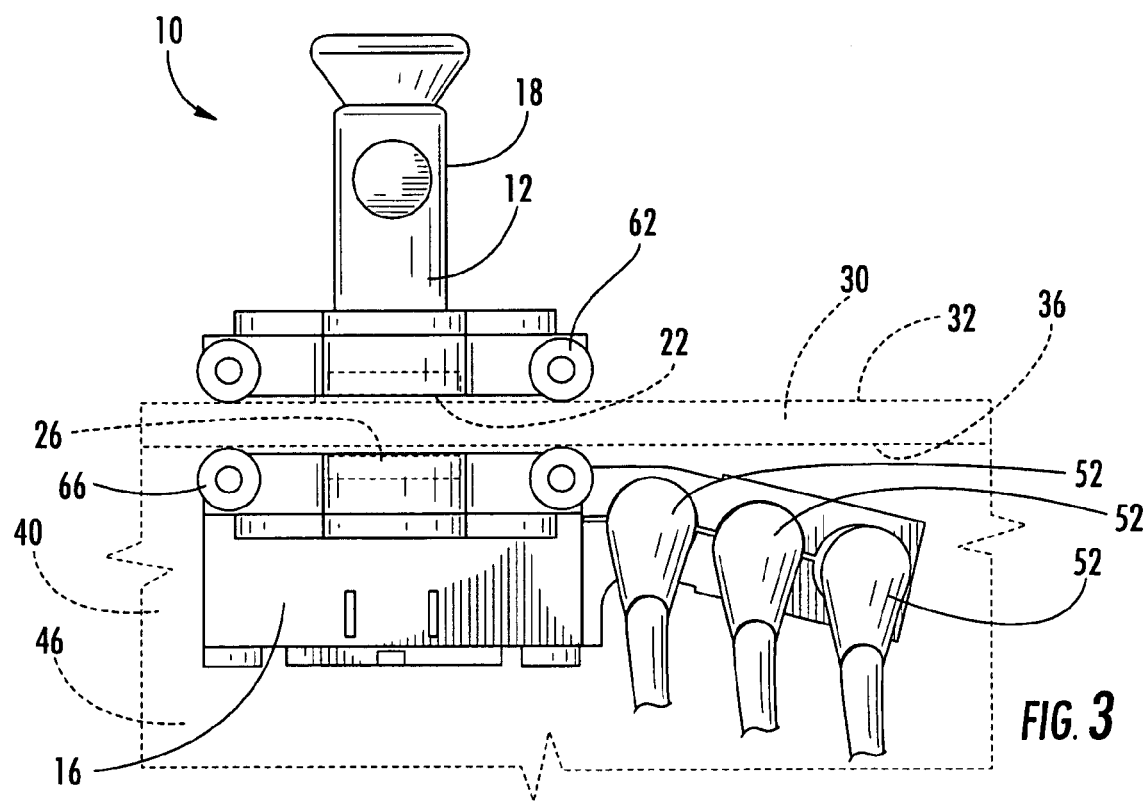
Figure 2:
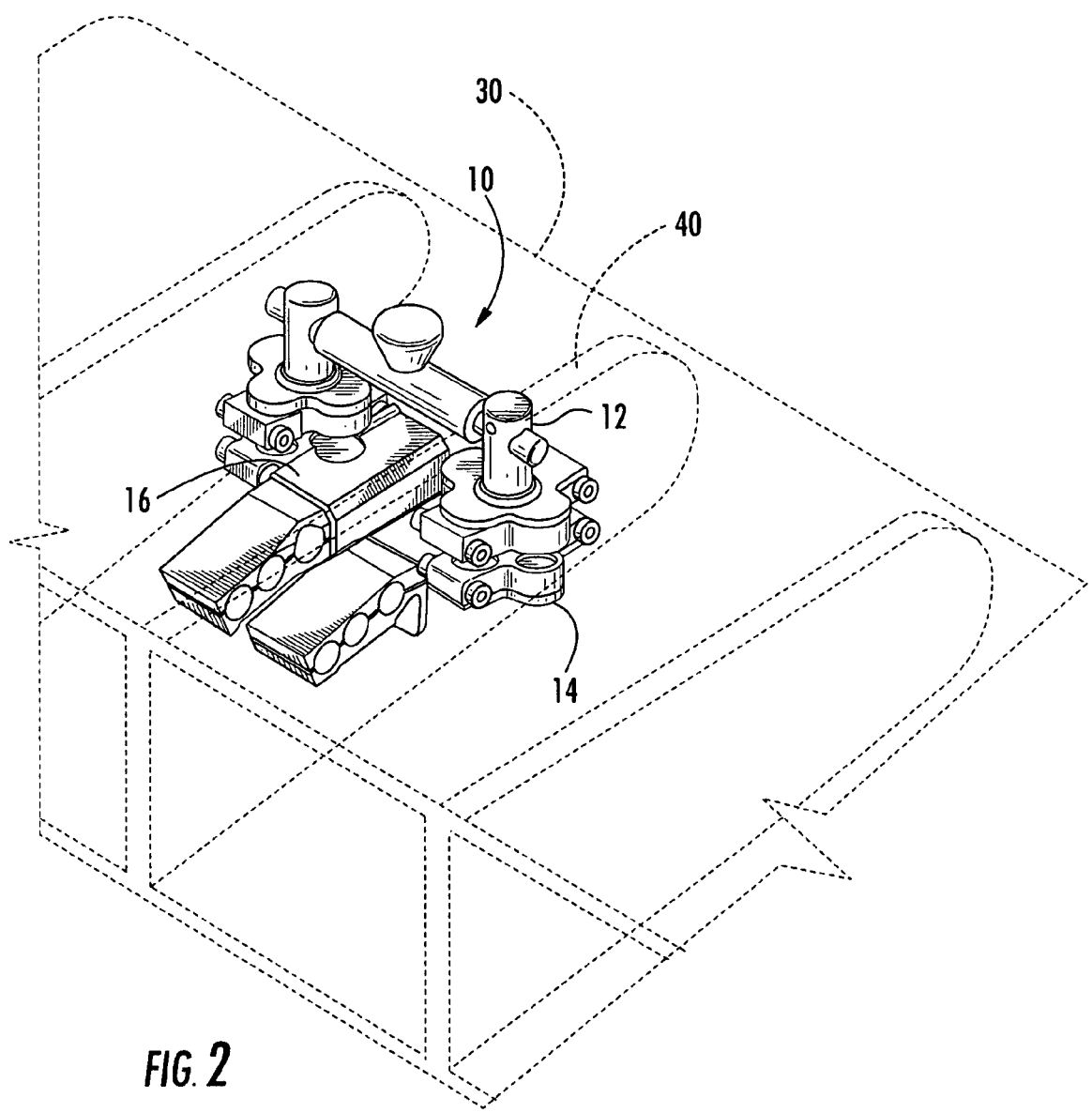
Figure 4:
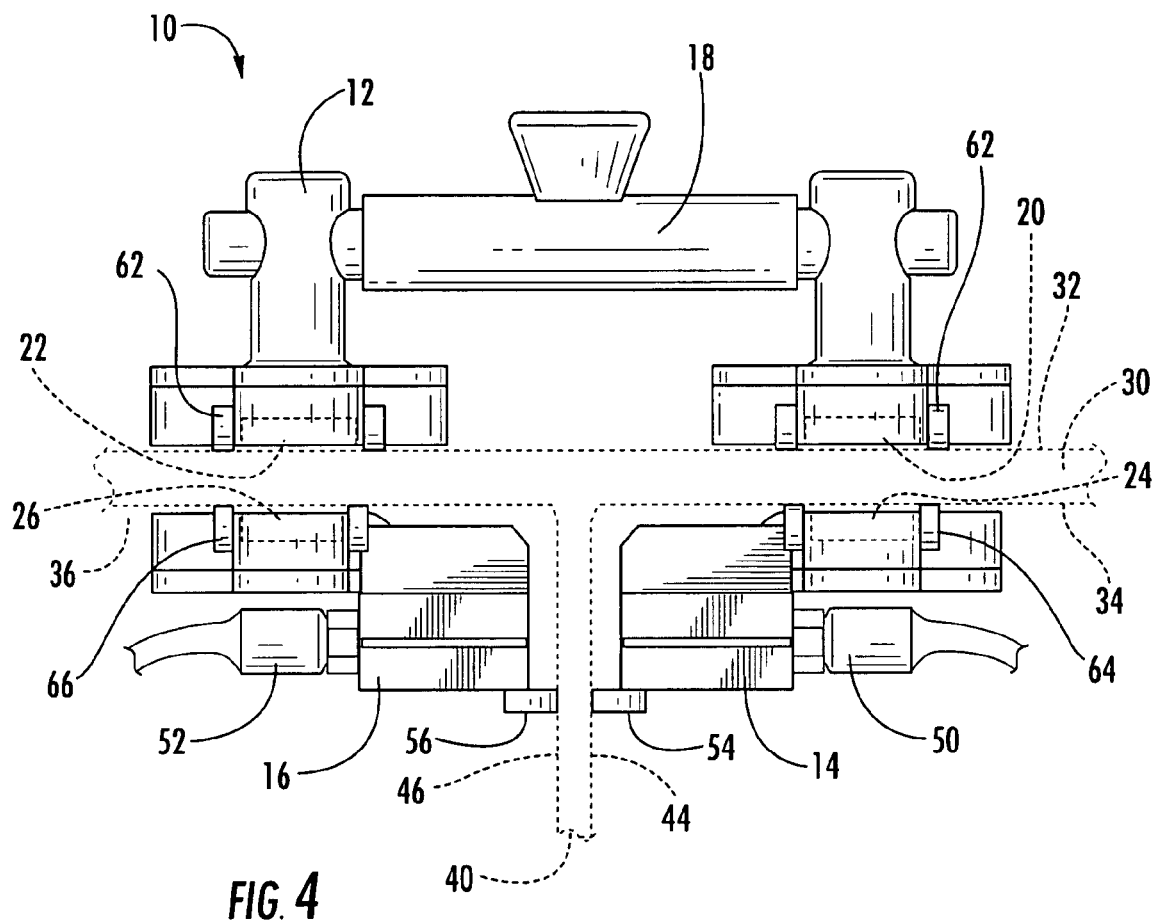
Figure 5:
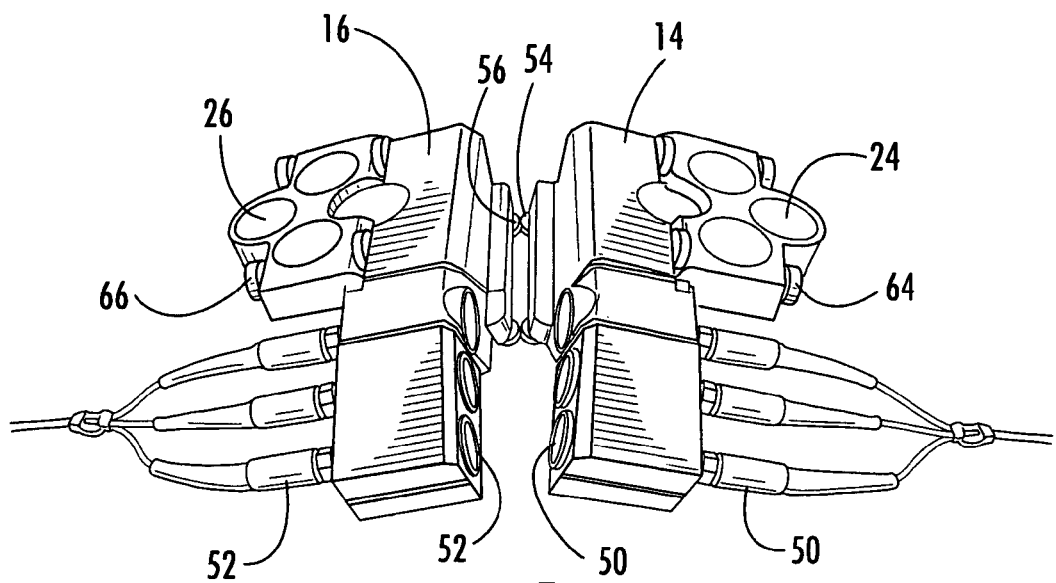
Figure 6:
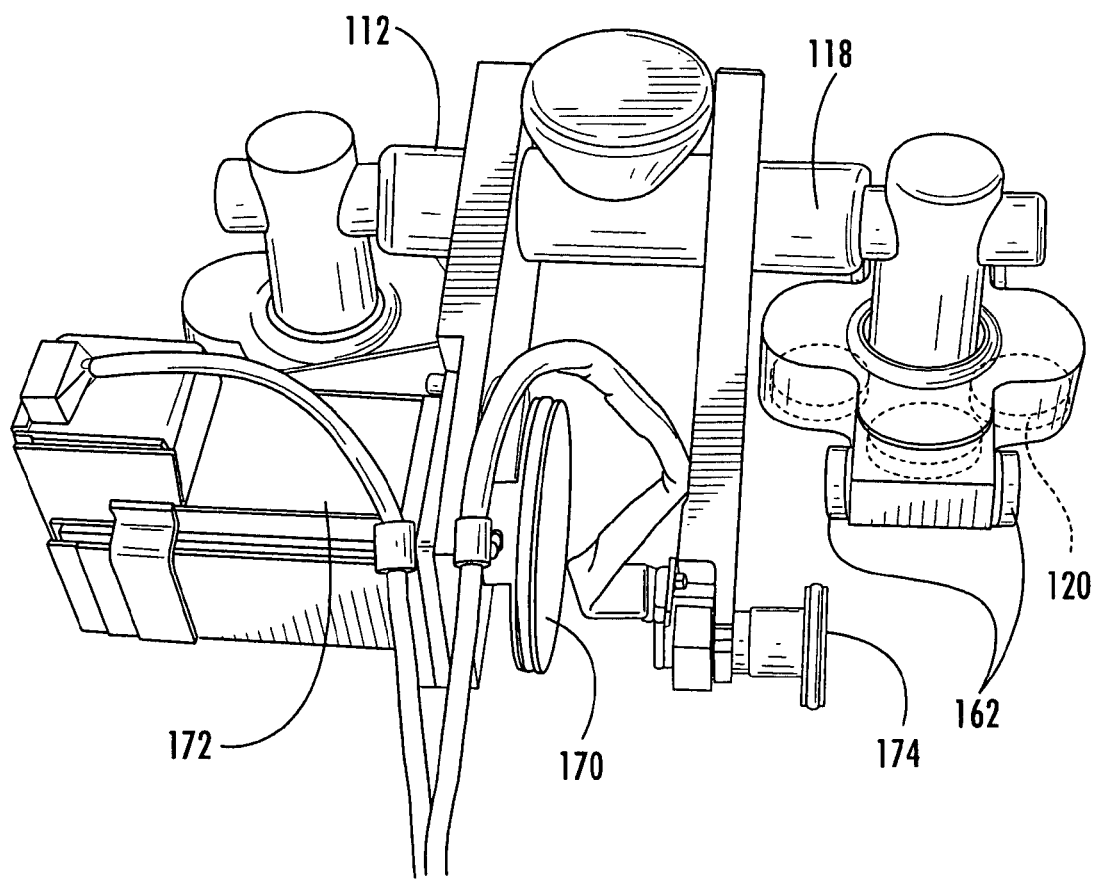
Figure 7:
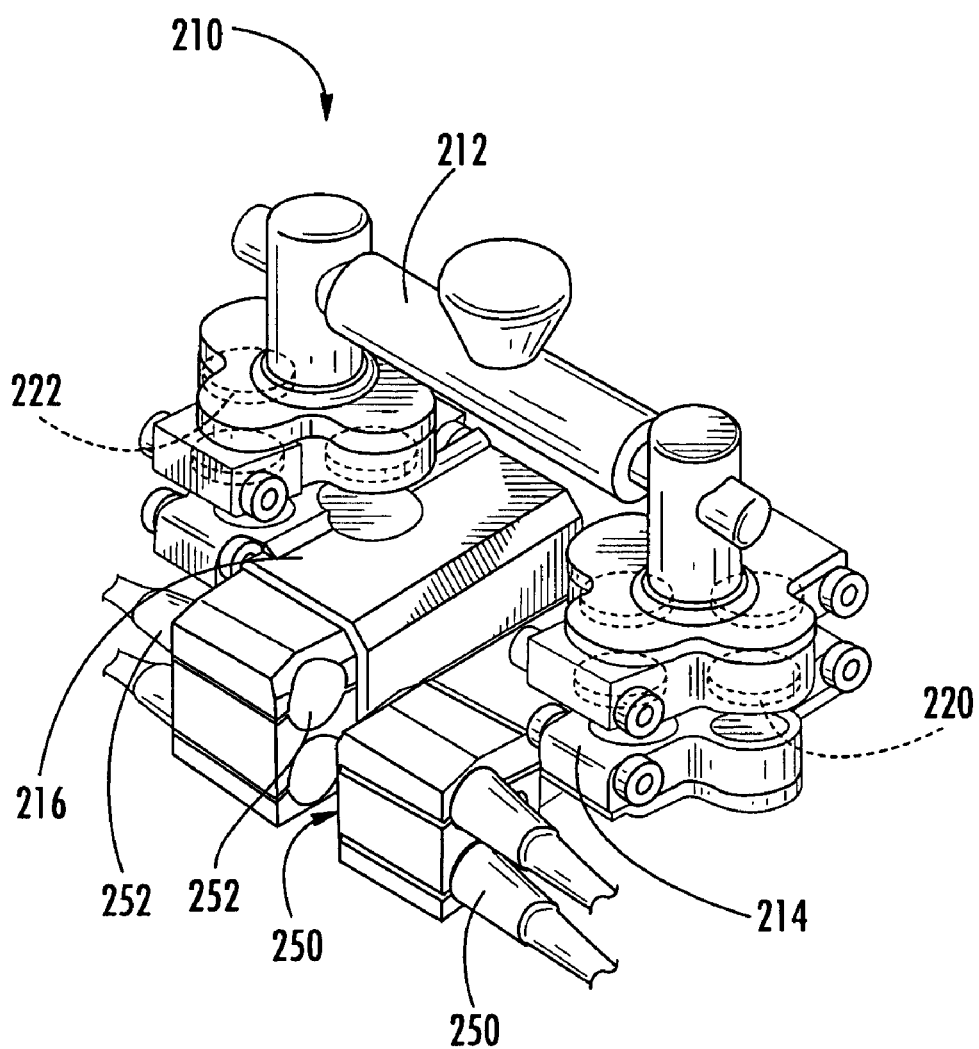
Figure 8:
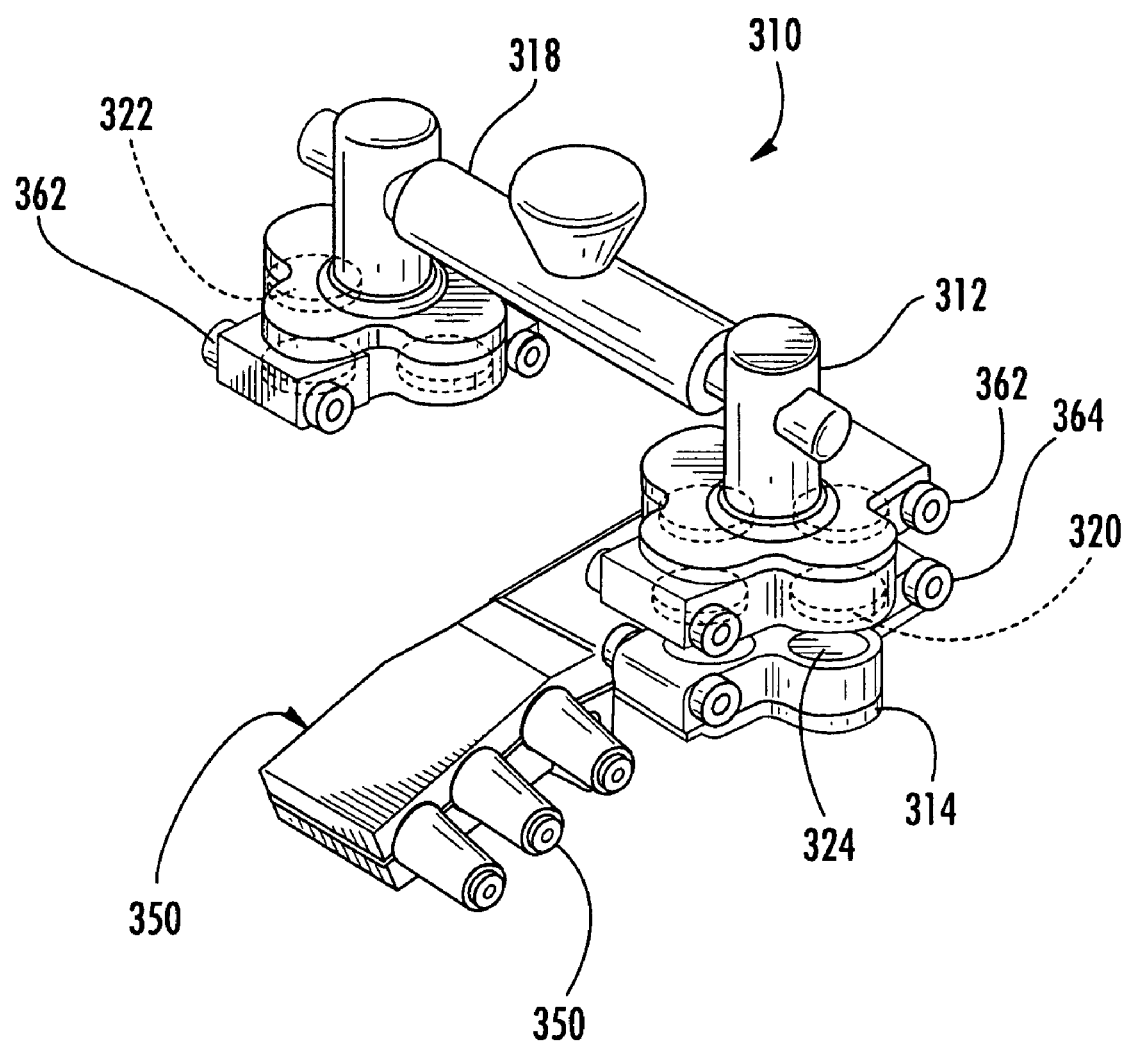
Figure 9:
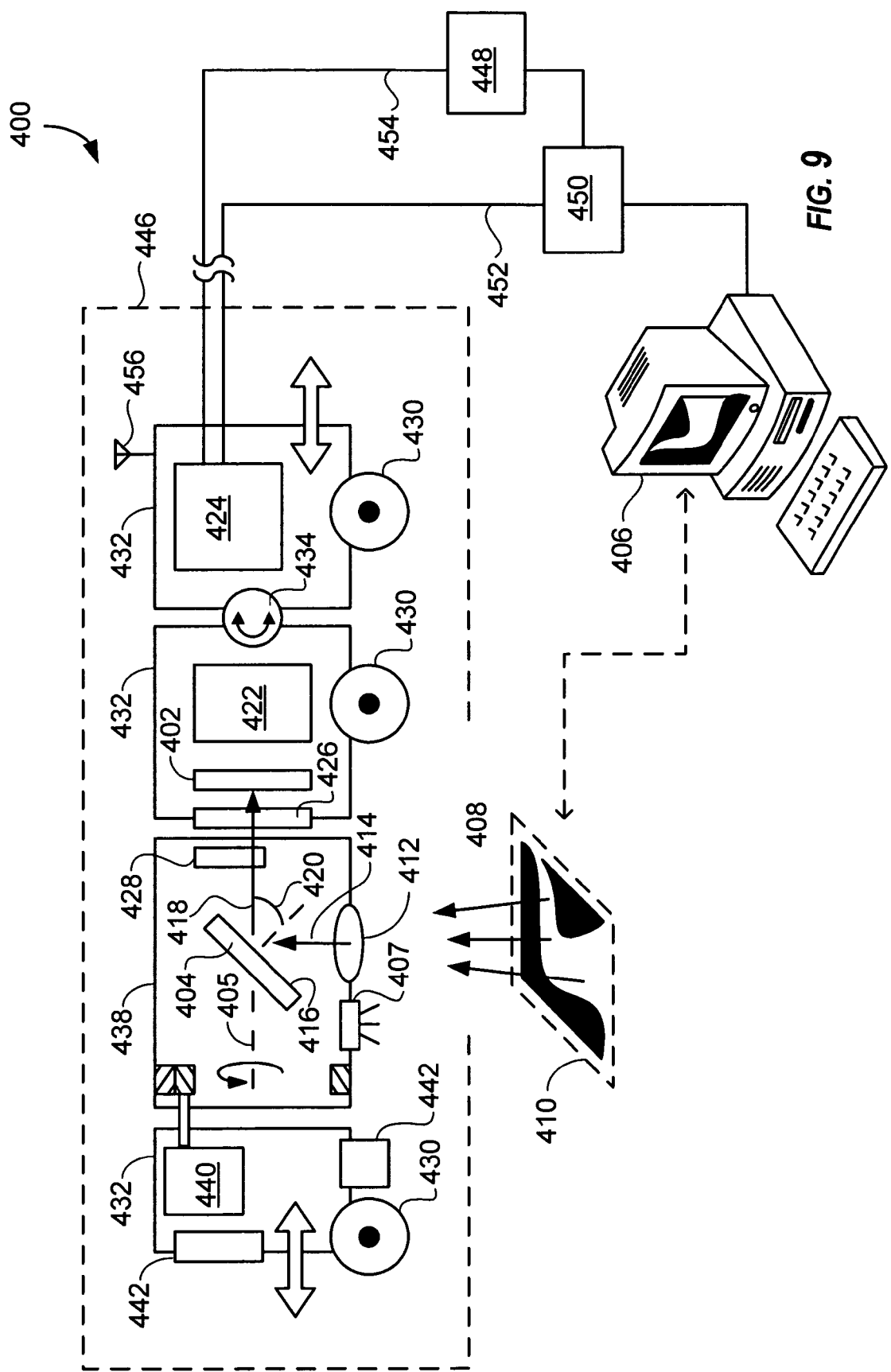
Figure 10:
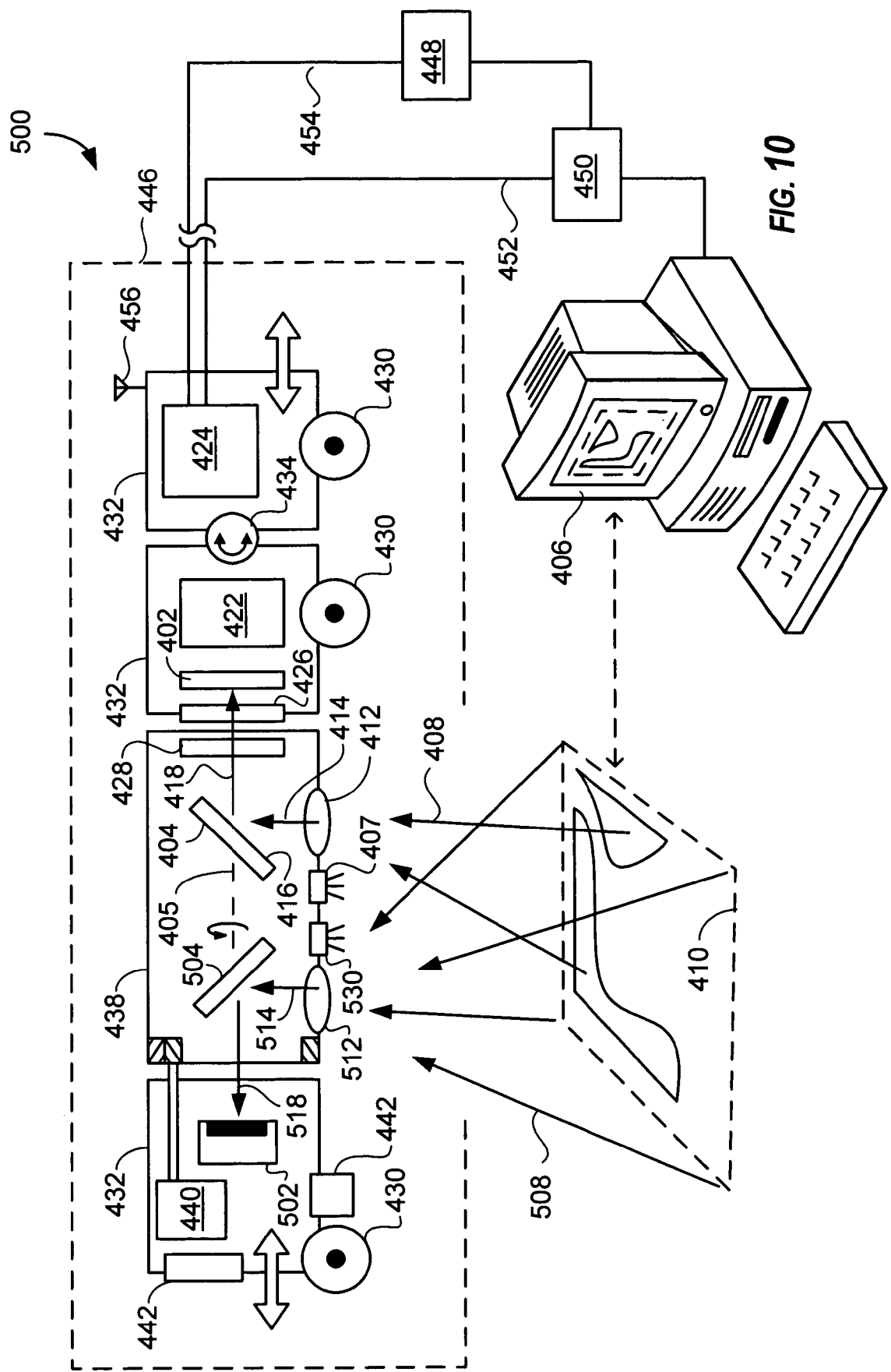
Figure 11:
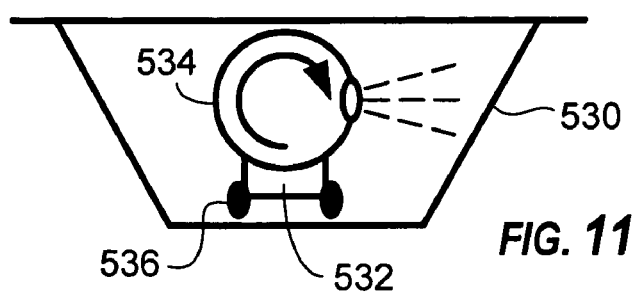
Figure 12:
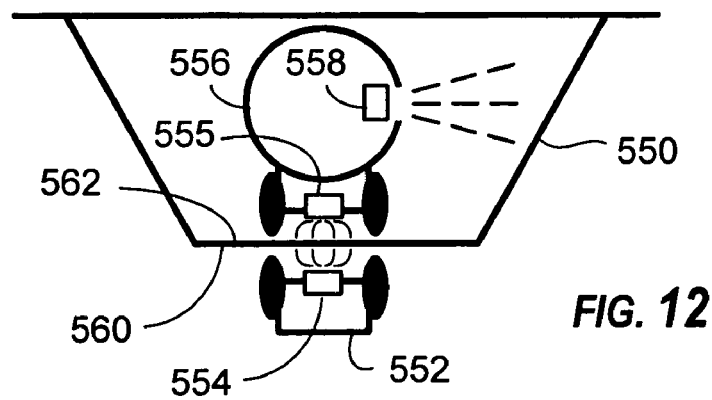
Figure 13:
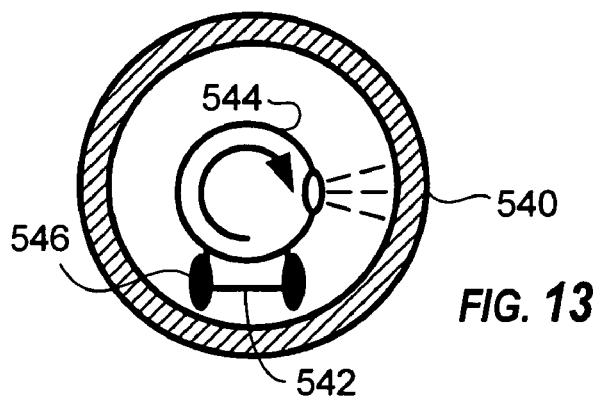
Figure 14:
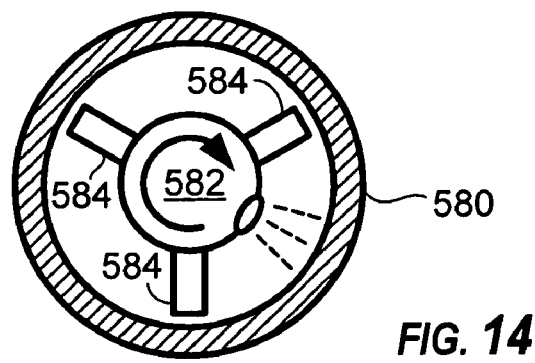
Figure 15:
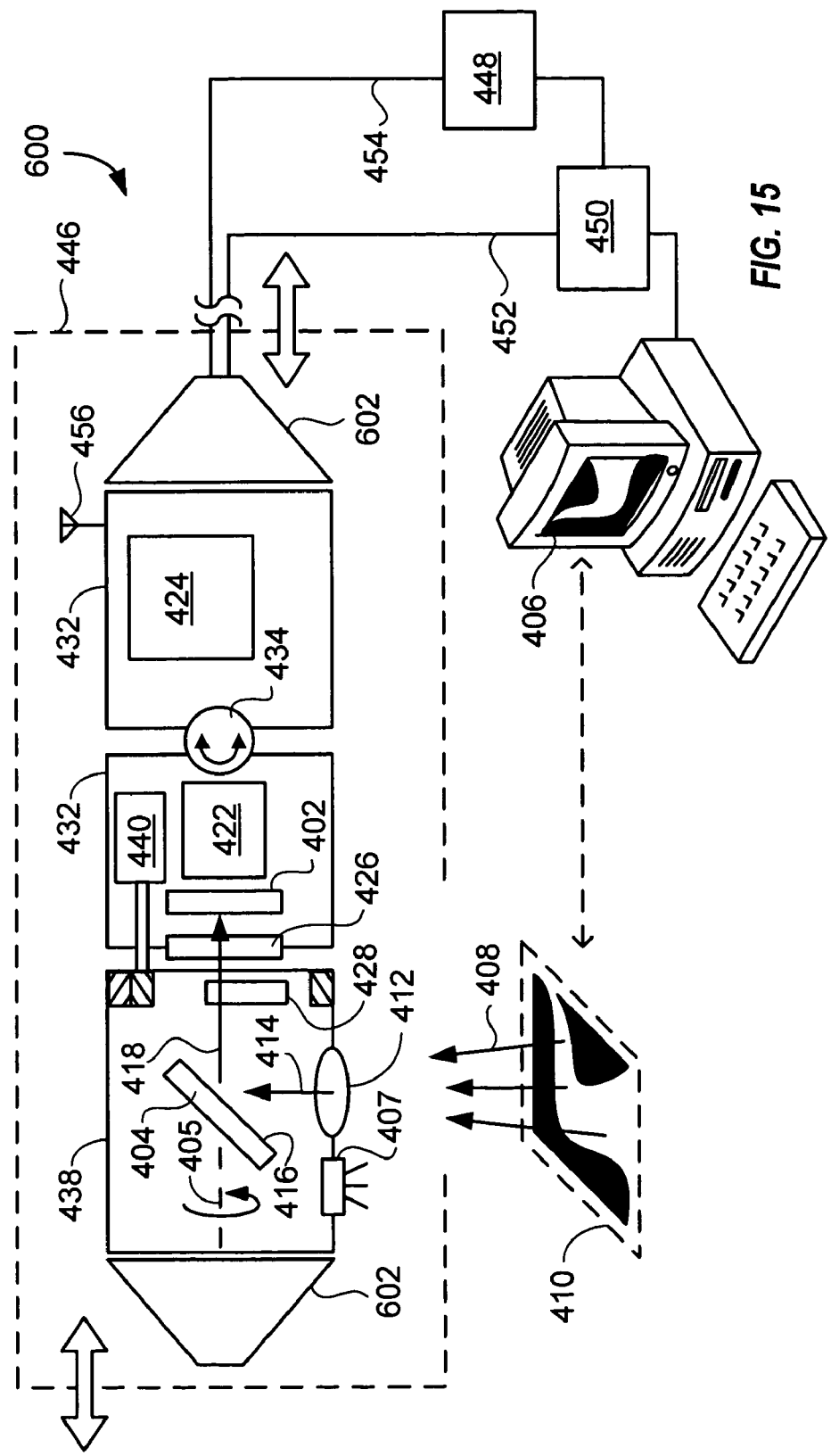

Having thus described the invention in general terms, reference will now be made to the accompanying drawings, which are not necessarily drawn to scale, and wherein:

FIG. 1 is a perspective view of a non-destructive inspection device in accordance with one embodiment of the present invention, illustrating an actuating portion and two inspecting portions;

FIG. 2 is an environmental view of the inspection device of FIG. 1, illustrating the inspection device positioned on a structure to inspect limited access features of the structure;

FIG. 3 is a side planar view of the inspection device of FIG. 1, illustrating the actuating portion on a first surface of a structure and one inspecting portion positioned on a surface opposite the first surface and suspended by the magnetic coupling between the actuating portion and the inspecting portion;

FIG. 4 is a rear planar view of the inspection device of FIG. 1, illustrating the actuating portion on a first surface of the structure and the two inspecting portions positioned on a surface opposite the first surface such that the feature of the structure to be inspected is located between the inspecting portions;

FIG. 5 is a top perspective view of the two inspecting portions of the inspection device of FIG. 1, illustrating the plurality of magnets and the array of inspection sensors on each inspecting portion;

FIG. 6 is a perspective view of an actuating portion of a non-destructive inspection device in accordance with a second embodiment of the present invention, illustrating an actuating portion that includes a motorized drive wheel and a positional encoder device;

FIG. 7 is a perspective view of a non-destructive inspection device in accordance with a third embodiment of the present invention, illustrating two inspecting portions having vertical arrays of inspection sensors;

FIG. 8 is a perspective view of a non-destructive inspection device in accordance with a fourth embodiment of the present invention, illustrating an inspection device with only one inspecting portion and with wireless inspection sensors;

FIG. 9 is a diagrammatic environmental view showing an infrared inspection system, according to an embodiment of the invention, that may provide infrared thermographic imaging;

FIG. 10 is a diagrammatic environmental view showing an inspection system, according to another embodiment of the invention, that may provide infrared thermographic imaging and visible light photographic imaging;

FIG. 11 is a diagrammatic environmental view showing an inspection device, according to an embodiment of the invention, providing non-destructive inspection of a partially enclosed space such as the interior of an aircraft fuselage hat stringer;

FIG. 12 is a diagrammatic environmental view showing an inspection device, according to another embodiment of the invention, having an inspection portion and an actuating portion magnetically coupled together and moving in concert along opposing surfaces of a structure;

FIG. 13 is a diagrammatic environmental view showing an inspection device, according to an embodiment of the invention, providing non-destructive inspection of a cylindrical conduit;

FIG. 14 is a diagrammatic environmental view showing a self-centering infrared inspection device, according to another embodiment of the invention, providing non-destructive inspection of a cylindrical conduit;

FIG. 15 is a diagrammatic environmental view showing an embodiment of the invention that may provide non-destructive inspections of limited clearance structures and conduits which may define pathways having turns and bends;

FIG. 16 is a diagrammatic environmental view showing an infrared inspection device having an inclining head, according to another embodiment of the invention, inspecting a structure that defines a partially enclosed space;

FIG. 17 is a diagrammatic environmental view showing an infrared inspection device, according another embodiment of the invention, having a mobile chassis capable of serpentine flexing for passage through enclosures having turns and bends; and FIG. 18 is a diagrammatic environmental view showing an infrared inspection device disposed on an elongate member, according to yet another embodiment of the invention, extended through an aperture to inspect a limited access area.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1-5, a non-destructive inspection device 10 in accordance with one embodiment of the invention is illustrated. The non-destructive inspection device 10 includes an actuating portion 12, a first inspecting portion 14, and a second inspecting portion 16. The actuating portion 12 and the inspecting portions 14 and 16 are individual portions and are not directly connected in the illustrated embodiment. The actuating portion 12 is structured for placement on a surface of the structure undergoing inspection. The inspecting portions 14 and 16 are structured for positioning on a surface opposite the surface the actuating portion is placed.

The actuating portion 12 includes at least one magnet, and optionally includes a plurality of magnets, such as four magnets in the illustrated embodiment, for magnetically coupling with each of the inspecting portions 14 and 16. The magnetic coupling provides a remote connection between the actuating portion 12 and the inspecting portions 14 and 16 so that the inspecting portions move in concert with the actuating portion. The actuating portions 14 and 16 move in concert with the actuating portion 12 such that the actuating portions maintain substantially consistent positions relative to the actuating portion while the inspecting portions are magnetically coupled to the actuating portion. The actuating portion 12 of FIG. 1 also includes a handle 18 that connects a first plurality of magnets 20 to a second plurality of magnets 22. The first plurality of magnets 20 magnetically couple with a plurality of magnets 24 of the first inspecting portion 14 during operation of the inspection device 10. Likewise, the second plurality of magnets 22 of the actuating portion 12 magnetically couple with a plurality of magnets 26 of the second inspecting portion 16 during operation of the inspection device 10. The first plurality of magnets 20 are magnetically coupled to the plurality of magnets 24 of the first inspecting portion 14 when the actuating portion 12 and the first inspecting portion are positioned on opposite surfaces of a structure 30, as shown in FIG. 4. The magnets are advantageously positioned such that the magnets are proximate the opposed surfaces 32 and 34 of the structure 30 such that the magnetic coupling therebetween is maximized. Similarly, the second plurality of magnets 22 are magnetically coupled to the plurality of magnets 26 of the second inspecting portion 16 when the actuating portion 12 and the second inspecting portion are positioned on opposite surfaces of the structure 30, as also shown in FIG. 4. The magnets are advantageously positioned such that the magnets are proximate the opposed surfaces 32 and 36 of the structure 30 such that the magnetic coupling therebetween is maximized, see for example, the U.S. Pat. No. 6,722,202 to Kennedy et al., issued Apr. 20, 2004 which is hereby incorporated herein by reference.

The magnets 20, 22, 24, and 26 of the illustrated embodiment, shown in FIGS. 1 and 5 are optionally pancake magnets formed of neodymium iron boron, which advantageously have greater magnetic flux (around 12,000 gauss) than standard ceramic or ferrite magnets (around 3,900 gauss). Although each plurality of magnets must comprise at least one magnet, the magnets of the illustrated embodiment are arranged in sets of four for a total of sixteen magnets included in the inspection device 10. Further embodiments of the invention may include magnets of different material, such as Samarium Cobalt or Alnico to list two non-limiting examples of alternative magnets, and/or may create the magnetic coupling with electromagnets or other magnetic coupling means. Embodiments of the present invention may further comprise magnetic shunting mechanisms to control the magnetic flux of the magnetic couplings, a non-limiting example being rare earth metal switched magnetic devices disclosed in U.S. Pat. No. 6,180,928 that is assigned to the present assignee.

Structures 30 that may be inspected with the inspection device 10 of the present invention may include but are not limited to composites, non-ferromagnetic metals (e.g. aluminum alloy, titanium alloy, or aluminum or titanium hybrid laminates such as GLARE or Ti/Gr), and polymers. It should be noted that the first surface 32, the surfaces 34 and 36, and the material therebetween, which collectively define the material through which the actuating portion 12 and the inspecting portions 14 and 16 are magnetically coupled, optionally comprise a non-ferromagnetic material because the magnetic coupling would be diminished or eliminated by a ferromagnetic material located between the actuating portion and the inspecting portions.

The pluralities of magnets support each inspecting portion 14 and 16 and keep each of the inspecting portions aligned. Each plurality of magnets 20, 22, 24, and 26 comprises at least one individual magnet and is not limited to four magnets each. Each plurality of magnets may also be arranged in any pattern, but the plurality of magnets that are to be aligned with and magnetically coupled to one another optionally have the same pattern for maximum coupling of the magnets.

Referring to FIGS. 2-4, the structure 30 includes a feature 40 that extends outwardly from the surfaces 34 and 36 of the structure, such as being perpendicular thereto. As shown in FIG. 2, the feature 40 of a structure 30 may be a limited-access feature such as a shear tie or spar that is bonded or fastened to the skin or joined to or protruding from the surfaces 34 and 36. The feature 40 may also include a pi joint connecting the feature to the surfaces 34 and 36, wherein the actual joint may be inspected by the inspection device 10. Alternative features to be inspected may be a feature of any shape, angular orientation, size, or location. The feature 40 of FIG. 4 represents an interior rib of a wing structure comprising a composite material for use in the aerospace industry; however, the feature 40 may represent any portion of any structure to be non-destructively inspected. Furthermore, the feature 40 may be of any material that may be non-destructively inspected, including ferromagnetic material. If no magnetic coupling is required through the feature 40 to be inspected, a structure 30 having a feature comprising a ferromagnetic material may be inspected if the material through which the actuating portion 12 and inspecting portions 14 and 16 are magnetically coupled comprises a non-ferromagnetic material. Such a structure 30 would typically be used for non-aerospace applications because of the importance of minimal weight in aerospace applications and a ferromagnetic feature 40 would usually be heavier than a non-ferromagnetic feature such as a composite feature. The inspection sensors used to inspect a ferromagnetic feature 40 optionally are impervious to the magnetic fields created by the magnetic couplings between the actuating portion and inspecting portions.

The feature 40 of the illustrated embodiment includes a first face 44 facing the first surface 34 and a second face 46 facing the second surface 36. When the inspection device 10 is positioned on the structure 30, as shown in FIG. 4, the feature 40 is located between the first inspecting portion 14 and the second inspecting portion 16. Further embodiments of the inspection device, such as the embodiment illustrated in FIG. 8, may include only one inspecting portion with at least one inspection sensor for non-destructive inspection of the feature 40, i.e., one-sided inspection relying on the reflection of signals from within the feature or viewing the feature with an optical borescope or miniature camera. One-sided ultrasonic inspection methods such as pitch catch, pulse echo, resonance, mechanic impedance, etc. are non-limiting examples of one-sided inspection techniques of further embodiments of the present invention comprising only one inspecting portion.

The first inspecting portion 14 and the second inspecting portion 16 of FIGS. 1-5 each include three inspection sensors. Further embodiments of the inspection device 10 may include any number of inspection sensors in various configurations. The first inspection sensors 50 of the first inspecting portion 14 are ultrasonic transmitters, while the second inspection sensors 52 of the second inspecting portion 16 are ultrasonic receivers. These inspection sensors 50 and 52 are advantageous because they do not require direct contact on the first face 44 and second face 46, respectively, of the feature 40 and do not require a couplant.

Alternative embodiments of the present invention may include other non-contact inspection sensors such as laser systems, optical borescopes, cameras, infrared sensors, and capacitive sensors, to list a few non-limiting examples.

To maintain a predefined distance between the inspection sensors 50 and 52 and the first face 44 and second face 46, respectively, of the feature 40 and to facilitate movement of the inspecting portions 14 and 16, rollers 54 and 56 are provided on the first inspecting portion 14 and the second inspecting portion 16, respectively, as shown in FIG. 4. The rollers 54 of the illustrated embodiment are located near the first plurality of magnets 20; however, further embodiments of the inspection device 10 may include rollers located at any position on the first inspecting portion 14, such as near the first inspection sensors 50. Likewise the rollers 56 of the second inspecting portion 16 may be located at any position on the second inspecting portion, but optionally mirror the rollers 54 of the first inspecting portion 14, as shown in FIG. 5. The rollers 54 and 56 also help maintain the alignment of the inspecting portions 14 and 16, respectively. The inspecting portions 14 and 16 may, alternatively, include skids, skis, or the like for maintaining the predefined distance and for facilitating movement of the inspecting portions over the feature 40.

Operation of the inspection device 10 consists of placing the actuating portion 12 on a first surface 32 of the structure 30 and positioning at least one inspecting portion, such as the first inspecting portion 14, on a surface 34 opposite the first surface such that the inspecting portion is proximate the feature 40 to be inspected. The magnets 20 and 24 of each portion 12 and 14, respectively, magnetically couple the inspecting portion to the actuating portion such that the inspecting portion is supported and aligned. To non-destructively inspect the feature 40, the inspection sensor 50 of the inspecting portion 14 is activated such that the signals received by the inspection sensor 50 are sent to a processing element for analysis and storage and, in one embodiment, for creating an output on a display that can be monitored by the technician. The displayed output, which may be data in any form such as numeric data or graphic data to list two non-limiting examples, advantageously represents the location and size of internal flaws or defects in the feature being inspected.

The actuating portion 12 is moved along the first surface 32 such that the inspecting portion 14 is correspondingly moved along the surface 34. The inspection device 10 of FIG. 1 may be manually moved by the technician who grasps the handle 18 to advance the actuating portion 12. The inspection device 10 is advanced along the length of the feature 40 to fully inspect the feature, such that the processed data is optionally collected for a summary of the overall inspection results to illustrate or indicate any flaws or defects in the inspected feature. After the feature 40 is sufficiently inspected, the inspection device 10 can be removed by pulling the first inspecting portion 14 from the structure 30 to overcome the magnetic couplings and then removing the actuating portion 12. Notably, the technician can inspect the feature 40 in a relatively blind manner since the technician generally does not need to access the surface 34 of the structure proximate the feature, other than to initially position the first inspecting portion 14 and to retrieve the first inspecting portion following the inspection.

The inspection device 10 may also be operated with two or more inspecting portions. The actuating portion 12 is placed on a first surface 32 of the structure 30, the first inspecting portion 14 is positioned on a surface 34 opposite the first surface, and the second inspecting portion 16 is positioned on a surface 36 that is also opposite the first surface such that the feature 40 to be inspected is located between the inspecting portions. The magnets of each portion magnetically couple the inspecting portions 14 and 16 to the actuating portion 12 such that the inspecting portions are supported by the actuating portion and aligned with the actuating portion. The inspecting portions 14 and 16 are also in generally fixed relative positions with respect to each other when each is magnetically coupled to the actuating portion 12. To non-destructively inspect the feature 40, the inspection sensors 50 and 52 of the inspecting portions 14 and 16, respectively, are activated such that the signals transmitted by the first inspection sensors 50 pass through the feature 40 and are received by the second inspection sensors 52 prior to being sent to a processing element for analysis and storage and, in one embodiment, for creating an output on a display that can be monitored by the technician. In other embodiments, an infrared sensor and an energy source are disposed on opposite sides of the feature 40 and the infrared sensor is adapted to detect thermal gradients generated in the feature by exposure to the energy source.

The actuating portion 12 is moved along the first surface 32 such that the inspecting portions 14 and 16 are correspondingly moved along the surfaces 34 and 36. The inspection device 10 of FIG. 1 may be manually moved by the technician who grasps the handle 18 to advance the actuating portion 12. The inspection device 10 is advanced along the length of the feature 40 to fully inspect the feature, such that the processed data is optionally collected for a summary of the overall inspection results to illustrate or indicate any flaws or defects in the inspected feature. After the feature 40 is sufficiently inspected, the inspection device 10 can be removed by pulling the inspecting portions 14 and 16 from the structure 30 to overcome the magnetic couplings and then removing the actuating portion 12. Similar to the inspection with one inspecting portion, the technician can inspect the feature 40 in a relatively blind manner since the technician generally does not need to access the surfaces 34 and 36 of the structure proximate the feature, other than to initially position the inspecting portions 14 and 16 and to retrieve the inspecting portions following the inspection.

A set of rollers 62, skids, skis, or the like may be provided on the actuating portion 12 to facilitate movement of the actuating portion and a set of rollers 64, skids, skis, or the like may be provided on the first inspecting portion 14 to facilitate movement along the surface 34. A set of rollers 66, skids, skis, or the like may also be included on the second inspecting portion 16 to facilitate movement along the surface 36. In the illustrated embodiment, the sets of rollers 62, 64, and 66 each include four individual rollers located near the plurality of magnets of each portion such that the magnets are nominally suspended above their respective surface, as shown in FIG. 4, so that the magnets do not contact the surface but maintain the magnetic coupling necessary to support and align the inspecting portions 14 and 16 such that the inspecting portions move in concert with the actuating portion 12 during the inspection of the structure. Further embodiments of the inspection device 10 may include sets of rollers, skids, skis, or the like at any location to facilitate movement of the portions of the inspection device or may include surfaces or features to facilitate the movement of the portions.

FIG. 6 illustrates an actuating portion 112 of a second embodiment of the inspection device of the present invention. The inspecting portions of the second embodiment of the inspection device are not shown to better illustrate the features of the actuating portion 112. The actuating portion 112 includes a motorized drive wheel 170 that is rotated by a motor 172 to provide for motorized positioning of the actuating portion 112 and the corresponding inspecting portions. The motorized drive wheel 170 allows a technician to control the inspection device from a terminal connected to the actuating portion and the inspecting portions so that the inspection device may be remotely controlled to generate data from the inspection sensors that may be processed and displayed, such as by a processing element. Therefore, the inspection device with the actuating portion 112 of FIG. 6 may be moved without manual contact by the technician, as required by the inspection device 10 of FIGS. 1-5. The drive wheel 170 of FIG. 6 contacts the surface of the structure that the actuating portion 112 is placed upon and advantageously includes a textured surface to provide sufficient friction so that the drive wheel does not slip relative to the surface of the structure. A motor power supply (not shown) operated by a technician or with automated equipment provides power to the motor 172 to rotate the drive wheel 170 either forward or backward as required to perform the inspection.

The actuating portion 112 of the inspection device of FIG. 6 also includes a positional encoder device 174. The positional encoder device 174 advantageously provides position data for the inspection device for more accurate or informative inspection results. The positional encoder device 174, which may be mounted to the actuating portion 112, as illustrated in FIG. 6, or to one or more inspecting portions of alternative embodiments (not shown), sends a signal to a processing element indicating the position of the actuating portion 112, or the inspecting portions, which corresponds to the location of the inspection device. The positional encoder device 174 may measure the movement or location of the actuating portion and/or the inspecting portion(s) to which it is attached relative to any surface of the structure or relative to any frame of reference integral to the structure or independent of the structure being inspected. The processing element that advantageously receives the signal from the positional encoder device 174 may correlate the signal from the positional encoder device to the signals received from the inspection sensors so that any detected defects or flaws are accurately located on the structure. The positional encoder device 174 of FIG. 6 is an encoder wheel that produces a signal that corresponds to the rotation of the encoder wheel that contacts the surface that the actuating portion 112 is placed upon, which further corresponds to the location of the inspection device. Further embodiments of the present invention may include a positional encoder device that alternatively measures the movement and/or location of the inspection device, a non-limiting example being an optical encoder that optically measures movement of the inspection device, for more accurate or informative inspection results.

FIG. 7 illustrates a third embodiment of the inspection device 210 that includes a first inspecting portion 214 and second inspecting portion 216, each having a vertical array of inspection sensors 250 and 252, respectively. Vertical arrangement of the inspection sensors 250 and 252 provides for additional inspection data during a single inspection iteration and allows inspection of areas further removed from the actuating portion 212. Further embodiments of the inspection device may have arrays of inspection sensors in any arrangement. Non-limiting examples include the horizontal arrangement shown in FIG. 4 or the angled arrangement shown in FIG. 3. In addition, the inspection sensors may be located on the inspecting portion at any position relative to the magnets of the inspecting portion.

FIG. 8 illustrates a fourth embodiment of the inspection device 310 of the present invention. The inspection device 310 of FIG. 8 comprises only one inspecting portion 314 that further comprises at least one inspection sensor 350 to perform one-sided inspections as described above. In addition, the inspection sensors 350 of FIG. 8 comprise wireless data transmission either directly or indirectly to the processing element. Examples of such wireless data communication include, but are not limited to, WiFi applications, Bluetooth applications, or other wireless LAN applications known in the art.

As detailed in the following descriptions with reference to at least FIGS. 9-18, a structure may be subjected to non-destructive inspection by use of an infrared sensor that detects infrared light radiating from the structure. Optionally, an infrared sensor collects data for infrared imaging and infrared thermography. Inspections without couplants, single-sensor multiple-sensor inspections, one-sided inspections, and inspections for irregularities at or below the surface of a material are all optionally available by infrared inspection. Furthermore, infrared inspections by a mobile infrared sensor may be conducted by remote control. Data may be collected, presented, and analyzed in real-time and may be stored for post-processing or later presentation. Presentations of data optionally include graphical representations that depict the inspected structure. Graphical representations related to infrared light and visible light may be displayed together in overlaid or tiled presentations.

FIGS. 9-18 relate to embodiments of infrared inspection systems for non-destructive inspection of structures, particularly structures having at least partially enclosed spaces such as internal conduits defined by hat stringers of aircraft fuselages and such as the interiors of pipes and ducts. For example, particular hat stringer configurations, materials of which hat stringers and other structures are composed, and inspections thereof are described in the co-pending U.S. non-provisional patent application No. 11/041,499, filed Jan. 24, 2005, the contents of which are incorporated herein by reference. When deployed in inspecting the conduit of a hat stringer, or when deployed in inspecting other types of bore structures and partially enclosed spaces, the infrared inspection systems according to the invention, some of which optionally include visible-light cameras or other optical devices, define optical borescopes. By collecting data from infrared (IR) light, and optionally visible light, inspection systems described herein may facilitate single-sided inspections with minimal contact with the inspected surface and without requiring couplants that are needed in some ultrasonic inspection systems. Where inspection systems described herein comprise arrayed sensors disposed at the focal planes of lens assemblies, high resolution imaging is facilitated, which imaging optionally includes infrared thermographic imaging and optionally includes visible light photographic imaging.

Infrared inspection systems according to various embodiments of the invention that are described herein, relate to the inspection of aircraft components and other structures as well. For example, structures having difficult-to-access areas, nuclear plant heating tubes, long gas and oil pipes, building shafts and conduits, fuel cell assemblies, automobile structures, petroleum and natural gas structures, and food processing facilities are all subject to infrared inspection according to the invention.

By way of infrared thermography, the infrared inspection systems according to some of the embodiments of the invention are capable of collecting data for generating viewable displays of thermal gradients that are indicative of features of the structure under inspection. In particular, generated displays facilitate the non-destructive identification of irregularities and flaws such as delaminations, disbonds, and fractures below the surface of the material of the structure and flaws such as scratches and holes defined at the surface.

With regard to features below a surface, including flaws that impart no evidence visible to the naked eye, flaws or damage such as voids, delaminations, and disbonds generally alter the heat characteristics of a material or structure. Temperature gradients detectable at the surface by IR thermography are often indicative of hidden irregularities or discontinuities. For example, a surface area above hidden damage will typically obtain a relatively cooler surface temperature indication when a heat source is behind a structure due to reduced heat flow through the damaged region. Conversely, the same surface area will typically obtain a hotter temperature surface indication when a heat source is on the same side of the structure as an IR sensor because dissipation of the applied heat is retarded by the damaged region. Thus, in-volume (below the surface) IR thermography can be achieved by near-side or far-side heating relative to the disposition of an IR sensor for non-destructive inspections of structures.

With regard to surface features, irregularities such as cracks, pits, scratches and holes generally affect the transport of energy across or along surfaces whether energy is being absorbed, radiated, or conducted. Thus, IR thermography is applicable to non-destructive in-volume inspections and surface inspections of a structure. For example, surface inspections wherein surface irregularities absorb energy from incident lasers and become cavity radiators are described in the U.S. Pat. No. 6,605,807 to Safai, issued Aug. 12, 2003, the contents of which are incorporated herein by reference.

FIG. 9 relates to an embodiment of the invention that may provide non-destructive inspection of a surface or structure by infrared inspection, which may include infrared thermographic imaging. As shown in FIG. 9, the infrared inspection system 400 comprises an infrared sensor 402, a rotatable reflector 404 disposed to reflect infrared light from an inspected surface to the infrared sensor 402, and a display system 406 communicably coupled to the infrared sensor for presenting data related to an output signal of the infrared sensor 402. The reflector 404 is rotatable about an axis 405 for receiving incident infrared light from a range of angular approaches disposed about the axis.

Thermal gradients may be naturally present in a structure inspected by the infrared inspection system 400 or may be generated by imparting energy into the structure. For example, the infrared inspection system optionally comprises an energy emitter 407 that directs energy onto an inspected structure for thermally exciting the structure thereby causing thermal gradients in the structure as heat dissipates therethrough. The emitter 407 optionally directs laser light on a structure as described in the U.S. Pat. No. 6,605,807 to Safai, issued Aug. 12, 2003. Laser light is optionally produced at the emitter 407 and is optionally produced elsewhere and conveyed to the emitter 407 by way of optical fibers. Furthermore, the emitter optionally comprises a heat source such as a heat lamp or hot air gun. The emitter is optionally disposed on or about the same side of the inspected structure as the infrared sensor 402 for near-side heating of the structure as shown in FIG. 9. Furthermore, an energy emitter is optionally disposed on or about another side of the inspected structure, such as a side opposing the infrared sensor 402, for far-side heating of the structure.

When the infrared inspection system 400 is in use, infrared light 408 is radiated by an area 410 of an inspected surface. The infrared inspection system 400 may further comprise an infrared lens assembly 412 through which the infrared light 408 passes when the infrared inspection system 400 receives infrared light.

The infrared lens assembly 412 optionally comprises of one more materials that transmit one or more infrared wavelength bands or spectral components thereof. For example, a mid-wavelength infrared (MWIR) band between 3 and 5 micrometers, and a long-wavelength infrared (LWIR) band between 8 and 12 micrometers are each generally transmitted by air. Thus, spectral components of these bands are often available for detection some distance from a heated structure. Therefore the infrared lens assembly optionally comprises materials that transmit the MWIR and LWIR bands, or spectral components thereof. Exemplary such materials include, but are not limited to: calcium fluoride; germanium; plastic; silicon; zinc selenide; and zinc sulfide. Furthermore, the infrared lens assembly optionally comprises sapphire, which transmits the short-wavelength infrared (SWIR) band between 1 and 3 micrometers, and optionally comprises quartz, which transmits both visible and infrared light.

The infrared lens 412 assembly optionally resides at or proximal the exterior of the infrared inspection system 400 and may therefore be subject to damage or degradation. Damage such as scratches and wearing of the surface may occur due to occasional unintended contact with other materials or equipment. Degradation may occur due to exposure to corrosive and solvent-rich conditions such as, with particular regard to hygroscopic calcium fluoride, moist environments. Therefore, one or more layers, overlays, or fixtures optionally protect the infrared lens assembly 412. For example, a protective diamond coating is optionally applied to one or more surfaces of the lens assembly for protection thereof.

The infrared lens assembly 412 optionally has a short focal distance for use in close proximity inspection of a surface, for use in inspecting the interior of a small confined space, and for use in one-to-one imaging. Various embodiments of infrared lens assemblies optionally comprise respectively fish-eye wide angle lenses and narrow angle lenses according to various respective uses thereof.

The infrared lens assembly 412 optionally comprises a number of elements that transmit and refract infrared light and that have adjustable relative dispositions such that the focal distance defined outwardly from the infrared inspection system 400 and the focal plane defined within the system are each adjustable. The infrared lens assembly 412 optionally comprises motorized components or remotely actuated components for facilitating automated or user-guided focusing.

The rotatable reflector 404 comprises a reflective surface 416. The reflective surface 416 may be a polished surface, and optionally comprises gold. Infrared light 414 passing through the infrared lens assembly 412, with or without refractive focusing by the lens assembly, is generally incident upon the reflecting surface 416. The reflecting surface 416 is angularly oriented from the axis 405 such that the infrared light 414 incident upon the reflecting surface is reflected as infrared light 418 generally toward the infrared sensor 402. The disposition of the infrared lens assembly 412 is generally fixed relative to the reflector 404 such that the lens assembly is rotatable with the reflector. As the reflector 412 is rotated, the lens assembly 406 exhibits a generally circular orbit about the axis 405 in a plane perpendicular to the axis.

Though other optical pathways are obtained in other embodiments of infrared inspection systems according to the invention, in the illustrated embodiment of FIG. 9, an optical pathway is defined by the infrared lens assembly 412, the reflector 404, and the infrared sensor 402, wherein the reflector is disposed in the optical pathway between the infrared lens assembly and the infrared sensor. Infrared light radiated by an inspected area of a structure follows the course of the optical pathway by transmitting and optionally refracting through the infrared lens assembly 412, reflecting from the reflector 404, and impinging upon the infrared sensor 402.

Though other relative angular orientations, relative dispositions, and focal arrangements are obtained in other embodiments of infrared inspection systems according to the invention, the reflecting surface 416 of the reflector 404 may be oriented at an angle 420 from the axis 405. In the embodiment illustrated in FIG. 9, the angle 420 is approximately forty five degrees. Furthermore, the infrared sensor 402 is optionally disposed on the axis 405 about which the reflector 404 is rotatable. The infrared lens assembly 412 may have a focal plane coincident with the infrared sensor 402 and, in at least one embodiment, is disposed to focus an infrared image of the inspected area 410 onto the infrared sensor 402 for graphical representation of the infrared image on the display system 406.

The infrared sensor 402 may comprise an infrared sensitive array, such as a focal plane array (FPA), for receiving an infrared image and generating an output signal that conveys the infrared image. For example, the infrared sensor 402 optionally comprises a two-dimensional array of infrared sensitive pixel cells disposed in a plane perpendicular to the axis 405. The infrared sensor 402 may comprise one or more materials or detectors sensitive to one or more of the SWIR, MWIR, and LWIR bands. Exemplary LWIR sensitive materials and detectors include, but are not limited to: barium strontium titinate, with regard to thermopile detectors and microbolometers; quantum well detectors, including layered detectors and wavelength specific detectors; and ferroelectric detectors. Exemplary MWIR sensitive materials and detectors include, but are not limited to: indium antimonide (InSb) detectors; and platinum silicide (PtSi) detectors. Exemplary SWIR sensitive materials and detectors include, but are not limited to: lead selenide (PbSe), sometimes referred to as "lead salt" detectors; and indium gallium arsenide (InGaAs) detectors. With regard to a sensor capable of detecting SWIR, MWIR, and LWIR radiation, mercury cadmium telluride (HgCdTe) is sensitive to infrared light in a broad spectral range.

The infrared inspection system 400 optionally comprises a cooling system 422 for cooling the infrared sensor 402 and for reducing noise in the detector or as may be beneficial some types of sensors. For example, mercury cadmium telluride detectors generally benefit with regard to noise reduction by cooling the detector whereas thermopile detectors may be operated with or without cooling. Exemplary cooling systems include, but are not limited to: thermoelectric systems; Joule-Thomson systems; and liquid nitrogen systems.

The infrared inspection system 400 optionally comprises an infrared window 426 for isolating the infrared sensor 402 and for protecting the sensor from exposure to such harmful elements as moisture. Insofar as the infrared sensor 402 is cooled, the infrared window isolates the sensor from environmental moisture that may otherwise condense on the sensor. The infrared inspection window 426 may be constructed of one or more materials that allow transmission therethrough of infrared light. Exemplary materials for constructing an infrared window include, but are not limited to: calcium fluoride; germanium; plastic; sapphire; silicon; zinc selenide; zinc sulfide; and quartz.

The infrared inspection system furthermore comprises a signal processor 424 for receiving output signals of the infrared sensor. The signal processor 424 generally receives analog signals that convey information about the infrared light 418 impinging upon the infrared sensor 402 and generates digital data based on the analog signals. Insofar as the infrared sensor 402 comprises an array for thermography imaging, the signal processor 424 receives an analog signal from each element of the array and generates a corresponding respective digital value. The signal processor 424 optionally comprises one or more amplifiers, a multiplexer (MUX), and one or more analog-to-digital converters (ADC), optionally in single chip form. The signal processor 424 optionally comprises a computing device or system, such as a personal computer or workstation.

The infrared inspection system 400 furthermore optionally comprises a calibration element 428 such as a calibration disk to facilitate calibration of the system, for example with regard to accurate radiometric measurements of the thermal gradients of the area 410 of an inspected surface. The calibration element 428 optionally is movable into and out of the optical pathway preceding the infrared sensor or is optionally disposed peripherally to pathway but within direct or indirect view of the infrared sensor. The calibration element 428 optionally comprises a thermometer read by the signal processor 424 for calibrating the digital conversion of data against an absolute temperature scale to effect calibrated thermographic imaging at the display system 406. Thermographic imaging and radiometric measurements by way of a thermopile infrared sensor, for example, are particularly improved with regard to accuracy by disposing a calibration disk in view of the sensor.

The infrared sensor system 400 furthermore comprises one or more carriage elements 430 by which at least the infrared sensor 402 and first rotatable reflector are mobile. For example, carriage elements 430 optionally comprise wheels, bearings, rollers, tread belts, skids, skis, or the like. The carriage elements 430 may comprise metallic or non-metallic components for contacting surfaces and objects upon which or along which the carriage elements travel. In the illustrated embodiment, the infrared sensor system 400 comprises one or more chassis elements 432 each comprising respective carriage elements 430. One or more articulating couplers 434 are optionally disposed between adjacent chassis elements for providing maneuverability and cornering of the coupled chassis elements 432.

A rotatable head 438 comprises at least the rotatable reflector 404 and is rotatable relative to chassis elements 432. The rotatable reflector 404 and optional infrared lens assembly 412 are rotated by the head 438. The head 438 may be rotated by an on-board motor 440 coupled to the head 438 by a linkage system, or may be rotated by a linkage system extending to a remote motor or other rotational driver such as a hand-driven crank or a handle. The rotatable head 438 optionally rotates continuously or intermittently in one rotational direction as the chassis elements 432 are moved along the interior of a closed space or conduit structure. Alternatively, the rotatable head 438 may execute partial rotations in alternating directions such that the interior of a conduit structure is scanned in a raster pattern defined by movements of the head along the axis 405 and partial rotations of the head about the axis.

The infrared inspection system 400 optionally comprises one or more couplings 442 for applying a motive force to the chassis elements 432. The chassis elements 432 and rotatable head 438 are optionally movable by the couplings 442. Exemplary couplings include, but are not limited to: universal joints; ball and socket joints; hooks and other attaching fixtures; towing elements; and magnets. In particular the chassis elements are optionally moved in concert with an actuating portion (see FIG. 6) by way of magnetic couplings.

A mobile chassis 446 of the infrared inspection system 400 is defined by the chassis elements 432 and rotatable head 438. The mobile chassis 446 is movable relative to the display system 406 for deployment in inspecting, for example, bore structures, partially enclosed spaces, and, for particular example, interior spaces of aircraft structures such as fuselage hat stringers. One or more of the carriage elements 430 are optionally motorized and articulated for steering such that the mobile chassis is remotely controllable from the location of the display system. In one embodiment, the mobile chassis 446 comprises a remote motorized borescope driven along inspected structures under the control of a human operator at the location of the display system 406. The infrared inspection system optionally further comprises a positional encoder for mapping infrared image data to coordinates and dimensions of an inspected structure.

A power supply 448 provides power to the mobile chassis 446 for the movements of the chassis, rotations executed by its elements, for powering the emitter 444, and for powering the signal processor 424. The power supply optionally comprises a battery system on-board the mobile chassis 446 and optionally comprises a connection to a standard AC electrical power outlet.

A control unit 450 provides for controlling the infrared inspection system 400 and particularly the movements and functions of the mobile chassis 446. The control unit is optionally interfaced with, a part of, or separate from the display system 406.

The mobile chassis 446 and on-board systems thereof such as the signal processor 424 are optionally disposed in communication with the control unit 450 and power supply 448 by way of one or more cabled connections 452, 454. The mobile chassis 446 further optionally comprises one or more wireless communication systems 456 for remote wireless deployment and control of the chassis and on-board systems thereof.

FIG. 10 relates to an embodiment of the invention that may provide non-destructive inspection of a surface or structure by both infrared inspection, which may include infrared thermographic imaging, and visible light inspection, which may include photographic imaging. In FIG. 10, wherein like reference numerals in FIGS. 9-10 relate to like elements, the inspection system 500 combines visible light inspection with the capabilities of the infrared inspection system 400 of FIG. 9. The infrared and visible light inspection system 500 thereby comprises a borescope for inspecting structures and may utilize both infrared thermography imaging and visible light video imaging. Visible light video imaging can entail both snapshot photography and motion picture imaging.

The infrared and visible light inspection system 500 comprises an optical device 502 that is sensitive to visible light and is disposed to collect visible light 508 from an inspected surface. For example, the optical device optionally comprises a charge-coupled device (CCD), a complimentary metal oxide semiconductor device (CMOS), or a line scan device. In the illustrated embodiment of the infrared inspection system 500, visible light 508 enters the rotatable head 438 through a visible-light lens assembly 512. Visible light 514 transmitted through the lens assembly is reflected as visible light 518 along the axis 405 by a rotatable mirror 504 that may rotate with the rotatable mirror 404. The visible light 518 impinges upon the optical device 502. The lens assembly generally has a focal plane coincident with the optical device 502 for graphical imaging of the inspected area 410. Optionally, a visible light source 530 illuminates the inspected area 410. Exemplary visible light sources include, but are not limited to: broad spectrum incandescent light sources; spectrally filtered incandescent light sources; gaseous discharge sources having broad spectra; single-species gaseous discharge sources having discrete spectral components; and light emitting diodes (LED). In particular, an LED comprising a doped phosphorescent coating is capable of emitting a visible light field relatively free of infrared spectral components, and is therefore useful in combining visible light imaging with infrared thermography by minimizing the potential for overwhelming an infrared sensor. The visible light source 530 is furthermore optionally strobed to be asynchronous with the infrared sensor 402 in order to minimize interference between the source 530 and the sensor 402.

The display system 406 presents data related to both the infrared light 408 and the visible light 508 from the inspected area 410. The display system optionally presents thermographic images, based on an output signal of the infrared sensor 402, and video images, based on an output signal of the optical device 502. Thermographic and video images may be superimposed as shown in FIG. 10.

Alternatively, thermographic and photographic images are separately presented. The display system optionally presents data in real time and optionally comprises a memory or storage device for storing data for later presentation or post-processing.

FIG. 11 relates to an infrared inspection device, according to an embodiment of the invention, that provides non-destructive inspection of a partially enclosed space defined by a structure 530 such as the interior of an aircraft fuselage hat stringer. In this embodiment, an infrared inspection device comprises a mobile chassis 532, a rotatable head 534, an on-board infrared sensor, and one or more motorized carriage elements 536. The mobile chassis 532 drives along the structure as an on-board infrared sensor collects data for infrared thermographic imaging.

FIG. 12 relates to an infrared inspection device, according to another embodiment of the invention, that comprises an actuating portion and an inspecting portion magnetically coupled together to move in concert along opposing surfaces of a structure. In FIG. 12, an infrared inspection device comprises an actuating portion 552 having at least one magnet 554, and an inspecting portion 556 having an infrared sensor 558 and optionally having a magnet 555. The actuating portion is placed on a first surface 560 of the inspected structure 550 and is movable relative to the structure. The inspecting portion is disposed on a second surface 562 of the structure that is opposite the first surface. The inspecting portion 556 is magnetically coupled to the actuating portion 552 causing the inspecting portion to move in concert with the actuating portion when the actuating portion is moved. The inspecting portion 556 moves along the second surface 562 when the actuating portion 552 moves along the first surface 560. The actuating portion 552 may be moved manually or by motorized locomotion. The inspecting portion 556 and actuating portion 552 optionally each comprise a plurality of magnets that cause the disposition of the inspecting portion relative to the actuating portion to be maintained. In FIG. 12, the structure 550 is illustrated to appear as a structural stiffener of an aircraft component for the purpose of providing an example. FIG. 12 nonetheless relates as well to other structures.

FIG. 13 relates to an infrared inspection device, according to an embodiment of the invention, that provides non-destructive inspection of a cylindrical conduit 540 such as a pipe. In this embodiment, an infrared inspection device comprises a mobile chassis 542, a rotatable head 544, an on-board infrared sensor, and one or more carriage elements 546. The mobile chassis 542 is movable along the conduit as the on-board infrared sensor collects data for infrared thermographic imaging. The rotatable head 544 is capable of rotating at least one full rotation for thorough inspection of the conduit.

FIG. 14 relates to a self-centering infrared inspection device, according to another embodiment of the invention, that provides non-destructive inspection of a cylindrical conduit 580, such as a pipe. In this embodiment, the mobile chassis comprises a rotatable head 582, an infrared sensor, and multiple self-centering carriage elements 584. The self-centering carriage elements 584 are optionally biased radially outwardly to contact the interior of the pipe 580 and promote centering of the mobile chassis within the pipe. The carriage elements 584 optionally comprise wheels, bearings, rollers, tread belts, rails, skids, skis, or the like. The self-centering carriage elements may define a centering spring assembly of the type described in the United States patent application publication number US2004/0189987A1 of Bondurant et al., published Sep. 30, 2004, the contents of which are incorporated herein by reference. The aforementioned reference recites that only non-metallic components be used where the described probe is in contact with a tube surface. Nonetheless, the carriage elements 584 of FIG. 13, and other carriage elements described herein, may comprise metallic or non-metallic components for contacting surfaces upon which or along which the chassis travels. Metallic components of the carriage elements 584 may provide advantages in contacting the pipe 580 or other structure. For example, a metallic component may provide durability for long service life and may provide an electrically conducting connection that may convey an electrical signal or may prevent the build-up of a static electrical charge.

FIG. 14 relates to one example wherein an infrared inspection device is lowered and raised within a vertical pipe by a tether or other elongate connector. FIG. 14 relates as well to another example wherein an infrared inspection device is pulled along a horizontal or partially inclined pipe by a tether or other elongate member. FIG. 14 also relates to yet another example wherein an infrared inspection device is pushed along a pipe by a rigid member or a flexible member.

FIG. 15 relates to an embodiment of the invention that may provide non-destructive inspections of limited clearance structures and conduits which may define pathways having turns and bends. In FIG. 15, wherein like reference numerals in FIG. 9 relate to like elements, the inspection system 600 defines a probe that is passively or actively articulated to go around corners and bends. The mobile chassis 446 of the infrared inspection system 600 comprises beveled end caps 602 for protecting the rotatable head 438 and chassis elements 432. The beveled end caps 602 further promote navigation and self-guidance of the rotatable head 438 and chassis elements 432 through limited clearance structures and conduits that may define pathways having turns and bends.

One or more articulating couplers 434 are optionally disposed between adjacent chassis elements 432 to allow flexing of the mobile chassis 446 as it travels through pathways having turns and bends. The articulating couplers 434 may be passive or active. A passive articulating coupler 434 may flex when torsional forces are applied about the coupler by adjacent chassis elements 432. Exemplary passive articulating couplers include, but are not limited to: universal joints, ball and socket joints, springs, flexible goose-neck assemblies, hooks and other attaching fixtures, towing elements, tethers, cords, chains, belts, lines, and magnets.

An active articulating coupler 434 may flex, extend, move, or actuate under the control of the signal processor 424, control unit 450, or human operator and may provide for steering of the mobile chassis 446 about corners and turns. An active articulating coupler 434 may comprise a steering section of the type described in the U.S. Pat. No. 4,790,294 to Allred et al., issued Dec. 13, 1988, the contents of which are incorporated herein by reference. An active articulating coupler 434 may comprise other elements that include, but are not limited to: steering ball and socket joints; hinging joints actuated by tensional members; gears and axles; rack and pinion assemblies; springs and tensional elements; and shape memory actuators. Furthermore, the control unit 450 may comprise a control handle and viewing screen assembly of the type described in the U.S. Pat. No. 5,373,317 to Salvati et al., issued Dec. 13, 1994, the contents of which are incorporated herein by reference.

FIG. 16 relates to an infrared inspection device, according to an embodiment of the invention, having an inclining inspection head. A mobile chassis 610 is shown deployed within a partially enclosed space defined by surfaces 612 of a structure. The chassis 610 is movable within the space for inspecting the surfaces 612 and structure. The mobile chassis 610 comprises chassis elements 614 disposed along an axis 616, a head 618, and articulating couplers 622 disposed between adjacent chassis elements. The head is rotatable about an axis 620 that can be inclined away from the axis 616 according to the disposition of an articulating coupler 622. By rotation and inclination, the head is controllably oriented to inspect the surfaces 612 at various perspectives. For example, in FIG. 16 the head 618 peers somewhat forward along an axis 624 that is not perpendicular to an inspected area of a surface 612. This is advantageous in that glaring reflections caused by on-board emitters, reflections that might otherwise blind or overwhelm on-board sensors, can be minimized or avoided.

FIG. 17 relates to an infrared inspection device, according another embodiment of the invention, having a mobile chassis capable of serpentine flexing for passage through enclosures having turns and bends. The mobile chassis 630 is shown deployed within a partially enclosed space such as a duct. The mobile chassis 630 is capable of serpentine flexing by way of articulating couplers 632 that allow adjacent chassis elements 634 to flex relative to each other. Serpentine flexing allows the mobile chassis 630 to navigate a ducts, conduits, and enclosures that have turns and bends.

FIG. 18 relates to an infrared inspection device, according to yet another embodiment of the invention, wherein an infrared inspection head 636 is coupled to an elongate member 638 by way of articulating couplers 640. The head 636 is extended through an aperture to inspect a limited access area. The disposition of the head 636 is controlled at least in part by way of movement of the elongate member 638 which may be flexible or rigid.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended That which is claimed:

1. An infrared inspection system comprising:
an infrared sensor device;
a first rotatable reflector disposed to reflect infrared light from an inspected subject to the infrared sensor device;
a display system communicably coupled to the infrared sensor device for presenting data related to an output signal of the infrared sensor device; and
an optical device that is sensitive to visible light and is disposed to collect visible light from an inspected subject.

2. An infrared inspection system according to claim 1, further comprising a second rotatable reflector disposed to reflect visible light from an inspected subject to the optical device.

3. An infrared inspection system according to claim 2, wherein the optical device is disposed to collect images of an inspected subject by the way of the second rotatable reflector.

4. An infrared inspection system according to claim 3, wherein the infrared sensor device is disposed to capture an infrared image of an inspected subject, wherein the optical device is disposed to capture a visible-light image of the inspected subject, and wherein the display system is communicably coupled to the infrared sensor device and to the optical device for presenting graphical representations of the infrared image and the visible-light image.

5. An infrared inspection system according to claim 1, further comprising one or more carriage elements by which at least the infrared sensor device and the first rotatable reflector are mobile.

6. An infrared inspection system according to claim 5, further comprising a coupling capable of applying motive force at least to the infrared sensor device and the first rotatable reflector for causing movement thereof.

7. An infrared inspection system according to claim 5, wherein the infrared sensor device and the first rotatable reflector are mobile relative to the display system.

8. An infrared inspection according to claim 5, further comprising:
motor operatively coupled at least to the one or more carriage elements for causing movement of at least the infrared sensor device and the first rotatable reflector; and
a controller operatively coupled to the motor for controlling movement of at least the infrared sensor device and the first rotatable reflector relative to the controller and display system.

9. An infrared inspection system according to claim 1, the optical device being disposed to capture a visible-light image of an inspected subject, the infrared sensor device being disposed to capture an infrared image of the inspected subject, the display system being communicably coupled to the infrared sensor device and to the optical device, and the display system being configured to present superimposed graphical representations of the infrared image and the visible-light image.

10. An infrared inspection system according to claim 1, further comprising a visible light source for illuminating an inspected subject, the visible light source configured to strobe asynchronously with the infrared sensor device.

11. An infrared inspection system according to claim 1, further comprising a visible light source capable of emitting visible light essentially free of infrared spectral components for illuminating an inspected subject.

12. An infrared inspection system according to claim 11, wherein the visible light source comprises a phosphorescent material.

13. An infrared inspection system according to claim 1, further comprising:
an actuating portion comprising a first magnet, the actuating structured for placement on a first surface of an inspected subject such that the actuating portion is movable relative to the inspected subject;
a second magnet; and
a mobile carriage upon which the infrared sensor device, the optical device, and the second magnet are disposed, the mobile carriage structured for positioning on a surface of the inspected subject opposite the first surface such that the mobile carriage is magnetically coupled to the actuating portion so that movement of the actuating portion causes the mobile carriage to move in concert with the actuating portion without the mobile carriage directly contacting the actuating portion.

14. An infrared inspection system according to claim 1, further comprising an infrared lens disposed to focus an infrared image of an inspected subject onto a focal plane coincident with the infrared sensor device, wherein the infrared sensor device comprises a focal plane array of infrared sensors.

15. An infrared inspection system according to claim 1, further comprising a wireless communication system by which the display system is communicably coupled to the infrared sensor device and to the optical device.

16. An infrared inspection system comprising:
an infrared sensor device;
a first rotatable reflector disposed to reflect infrared light from an inspected subject to the infrared sensor device;
a display system communicably coupled to the infrared sensor device for presenting data related to an output signal of the infrared sensor device;
a second rotatable reflector;
a camera device disposed to collect visible-light images of an inspected subject by the way of the second rotatable reflector; and
a mobile carriage upon which are disposed the infrared sensor device, the first rotatable reflector, the second rotatable reflector, and the camera device;
wherein the display system is communicably coupled to the infrared sensor device for presenting graphical representations of infrared images of an inspected subject,
wherein the display system communicably coupled to the camera device for presenting graphical representation of the visible-light images, and
wherein the mobile carriage is movable relative to the display system.

17. An infrared inspection system according to claim 16, the display system being configured to present superimposed graphical representations of the infrared images and the visible-light images.

18. An infrared inspection system according to claim 16, further comprising a visible light source for illuminating an inspected subject, the visible light source configured to strobe asynchronously with the infrared sensor device.

19. An infrared inspection system according to claim 16, further comprising a visible light source capable of emitting visible light essentially free of infrared spectral components for illuminating an inspected subject.

20. An infrared inspection system according to claim 19, wherein the visible light source comprises a phosphorescent material.

21. An infrared inspection system according to claim 16, further comprising:
   an actuating portion comprising a first magnet, the actuating portion structured for placement on a first surface of an inspected subject such that the actuating portion is movable relative to the inspected subject;
   a second magnet disposed on the mobile carriage, the mobile carriage structured for positioning on a surface of the inspected subject opposite the first surface such that the mobile carriage is magnetically coupled to the actuating portion so that movement of the actuating portion causes the mobile carriage to move in concert with the actuating portion without the mobile carriage directly contacting the actuating portion.

22. An infrared inspection system according to claim 16, further comprising an infrared lens disposed to focus an infrared image of an inspected subject onto a focal plane coincident with the infrared sensor device, wherein the infrared sensor device comprises a focal plane array of infrared sensors.

23. An infrared inspection system according to claim 16, further comprising a wireless communication system by which the display system is communicably coupled to the infrared sensor device and to the camera device.

* * * * *